United States Patent [19]

Frensch et al.

[11] 4,244,836

[45] Jan. 13, 1981

[54] PROCESS FOR MANUFACTURING MICROCAPSULES OF POLYVINYL ALCOHOL WITH LIQUID WATER-INSOLUBLE CONTENT

[75] Inventors: Heinz Frensch, Frankfurt am Main; Rudolf Heinrich; Konrad Albrecht, both of Kelkheim, all of Fed. Rep. of Germany

[73] Assignee: Hoechst Aktiengesellschaft, Frankfurt am Main, Fed. Rep. of Germany

[21] Appl. No.: 9,682

[22] Filed: Feb. 5, 1979

[30] Foreign Application Priority Data

Feb. 7, 1978 [DE] Fed. Rep. of Germany ....... 2805106

[51] Int. Cl.$^3$ ............................................. B01J 13/02
[52] U.S. Cl. ....................................... 252/316; 8/526; 71/64 F; 252/182; 252/188.3 R; 252/385; 252/388; 424/19; 424/33
[58] Field of Search ........................... 252/316; 424/33

[56] References Cited

U.S. PATENT DOCUMENTS

| 3,323,922 | 6/1967 | Durst | 426/89 |
|---|---|---|---|
| 3,582,495 | 6/1971 | Emrick | 252/316 |
| 3,584,113 | 6/1971 | Takebe et al. | 424/33 X |
| 3,627,693 | 12/1971 | Scarpelli | 252/316 |
| 3,664,963 | 5/1972 | Pasin | 252/316 |

OTHER PUBLICATIONS

Angewandte Chemie International Edition in English, vol. 14, (1975) No. 8, pp. 541, 542, 547 and 548.

*Primary Examiner*—Richard D. Lovering
*Attorney, Agent, or Firm*—Curtis, Morris & Safford

[57] ABSTRACT

Microcapsules having a shell consisting of water-soluble polyvinyl alcohol and containing a liquid, water-insoluble material are obtained by dispersing a liquid, water-insoluble phase of a substance, substance mixture or substance solution in an aqueous phase of polyvinyl alcohol obtained by partial hydrolysis of polyvinyl acetate and having a degree of hydrolysis of from 72 to 99 mol % and dehydrating the dispersion to obtain the capsules in powder form.

8 Claims, No Drawings

PROCESS FOR MANUFACTURING MICROCAPSULES OF POLYVINYL ALCOHOL WITH LIQUID WATER-INSOLUBLE CONTENT

This invention relates to microcapsules having a shell of water-soluble polyvinyl alcohol and a liquid, water-insoluble content, and to a process for the manufacture of such micro-capsules.

In recent years the technique of microencapsulation has gained in importance, since this method makes it possible to enclose substances of different states of aggregation in capsules made of inert material. Many mechanical and chemical processes for the manufacture of capsules have been described and are being used (cf. I. E. Vandegaer "Microcapsulation", Plenum Press, New York - London; 1974).

Microcapsules are being used as carriers for many different substances such as inks and dyes, pharmaceutical preparations, chemical reagents and the like, and attempts have been made repeatedly to microencapsulate plant protecting agents.

It is especially important to encapsulate toxic plant protecting agents or pesticides with regard to the safety of handling.

Another special advantage of the encapsulation of active substances is the possibility to combine substances that cannot be blended or are incompatible with one another. Thus, different active substances that would react with one another or change by external influences, for example by hydrolysis or oxidation, could be encapsulated separately and then mixed with one another.

Hitherto, it was often impossible to combine active substances that are incompatible with one another or they had to be stored separately and then blended directly prior to application, for example in the case of plant protecting agents in the spray tank. A further advantage of encapsulation resides in the fact that the active substance can be released in delayed manner to obtain a depot effect. In many cases, however, it is desirable or necessary to release the encapsulated active or other substances rapidly and completely in simple manner during application, preferably by means of water. It is, therefore, the object of the present invention to find an appropriate solution of this problem.

It has been proposed to encapsulate hydrophobic, oily liquids in an encapsulation material consisting of gelatin gum arabic/carboxymethyl cellulose (cf. DE-OS No. 2,027,819). The microcapsules obtained in this manner are, however, stable in water and release their content very slowly only.

In DE-OS No. 2,103,528 a process is described for producing small capsules the wall of which consists of several layers, for example, an inside layer of polyvinyl alcohol and an outside layer of gelatin. These capsules, too, can be rendered sufficiently soluble only by a several hour treatment with water.

U.S. Pat. No. 3,016,308 describes the manufacture of pulverulent formulations of microcapsules which may contain an oily liquid and which are obtained by spray-drying a film-forming polymer in the presence of the finely divided material to be encapsulated. As wall-forming polymers, polyacrylates, polyester resins, furane resins, polyurethanes, polyureas, polyamide, vinyl acetate polymers and cellulose derivatives are proposed.

Except for the products obtained with the various cellulose derivatives, all polymers are sparingly soluble or even insoluble in cold water. When dispersed in water, even the microcapsules made from hydromethyl, hydroxyethyl, carboxymethyl or methyl cellulose derivatives require very long swelling and dissolution times. Moreover, in many cases, the swelling of the cellulose particles clogs the nozzles of the application devices, for example sprayers.

It is, therefore, the object of the invention to formulate hydrophobic, water-insoluble substances, for example plant protecting agents, especially those that would undergo modifications in the presence of other substances or by external influences, by masking while avoiding the known difficulties and disadvantages, in such a manner that the active substances, for example plant protecting agents, are released under the action of water within a short period of time in a form suitable for application at the moment of application in the field. This is only possible by encapsulating the active ingredients in a substantially inert, film-forming substance which dissolves in water within a sufficiently short time. It has been found that water-soluble cellulose and starch derivatives yield products that dissolve slowly only in water and swell, whereas various types of polyvinyl alcohol surprisingly comply with the requirements. It was, therefore, the task of selecting from among the known types of polyvinyl alcohols those having optimum properties as regards film formation and water solubility and causing no troubles in the encapsulation of the active substances, for example by formation of agglomerations of individual capsules.

It is, therefore, the object of the present invention to provide microcapsules with liquid, water-insoluble content which are characterized in that the walls of the capsules consist of water-soluble polyvinyl alcohol.

It is another object of the invention to provide a process for the manufacture of microcapsules of encapsulating liquid, water-insoluble substances, substance mixtures and substance solutions, which comprises dispersing the liquid, water-insoluble phase in an aqueous polyvinyl alcohol solution and dehydrating the dispersion to obtain a powdery product of capsules.

The dispersion is preferably carried out at a temperature of from 10° to 80° C., more preferably 20° to 60° C.

To dehydrate the dispersion, spray drying proved to be especially suitable, preferably with air inlet temperatures in the range of from 120° to 150° C. It is also possible, of course, to remove the water in a different way. The resulting, dry and powdery product having good flow properties can be readily redispersed in water whereby the encapsulated content is set free in dispersed form and very stable, possibly opaque, dispersions or emulsions are obtained.

Substances that can be encapsulated are, in general, all liquid, water-insoluble substances, substance mixtures or substance solutions, for example pesticidal substances, substance mixtures or their solutions in inert organic solvents, pharmaceutical products or preparations, dye-stuffs, inks, chemical reagents, mineral oils, auxiliaries for metal working, anticorrosion agents. Best results are obtained with pesticidal substances, substances mixtures or solutions thereof as used in plant protection, to combat pests or in the chemical-technical field.

The liquid, water-insoluble phase to be used in the process of the invention consists of the water-insoluble substances to be encapsulated, for example an active substance, substance mixture or a solution thereof in an inert solvent immiscible with water, in a concentration of from 1 to 90, preferably 20 to 80, more preferably 40 to 70% by weight. Suitable solvents are compounds that are immiscible with water such as aromatic, aliphatic or cycloaliphatic hydrocarbons, alcohols, esters, ethers, or ketones, especially those having a boiling point above that of water, this fact being of importance, for example, in the spray-drying of the dispersion, such as xylenes, methylnaphthalenes, dimethylnaphthalenes, paraffin oils, cyclohexanone, 4-methylcyclohexanone, cyclohexanol, i-octanol, acetic acid heptyl ester, ethyl glycol acetate, butyl diglycol acetate, isophorone, or rape oil. In the case of mixtures of active substances, liquid active substances may serve as solvent for other active substances. The liquid phase immiscible with water may further contain solid constituents in finely dispersed form, for example active substances, dyestuffs or pigments.

According to the invention, the aqueous phase consists of a polyvinyl alcohol solution, preferably containing 2 to 50% by weight, more preferably 10 to 30% by weight of a polyvinyl alcohol (PVA) prepared by partial hydrolysis of polyvinyl acetate and having a degree of hydrolysis of 72 to 99 mol % and a viscosity of 2 to 18 centipoises, measured in a 4% aqueous solution at 20° C. in accordance with DIN 53 015. It proved advantageous to use partially saponified polyvinyl alcohols having a degree of hydrolysis of 83 to 88 mol % and a low viscosity, preferably of from 3 to 5 cP.

PVA types of high viscosity can also be used although the walls of the capsules made therefrom may dissolve in water more difficultly, i.e. more slowly, than the walls made from PVA types of lower viscosity. Above all when using PVA types of higher viscosity it might prove advantageous to add further components capable of modifying the properties of PVA films, for example polyethylene glycols, glycerol or trimethylol propane, in an amount of from 2 to 50, preferably 5 to 10% by weight, calculated on the PVA.

The wall thickness, tenacity and dissolution properties of the walls of the capsules depend on the amount and type of PVA used and of the modifying agent added, if any. It should also be kept in mind that the solubility of the polyvinyl alcohol capsules could be impaired by additional variables such as thermal treatment or the action of certain acids, salts or aldehydes. Thus, the solubility of PVA in water can be distinctly reduced by the action of ammonium chloride, sodium or ammonium dichromate, boron compounds, formaldehyde or glyoxal.

To prepare the polyvinyl alcohol solutions, solid, granular polyvinyl alcohol is strewn into water while stirring until dissolution is complete, optionally with heating to 80° to 95° C. as the dissolution proceeds the more rapidly the higher the temperature.

To carry out the process of the invention the liquid, the water-insoluble phase is first mixed with the aqueous polyvinyl alcohol solution which may contain further constituents. The proportion of the water-insoluble phase can amount to 20 to 80, preferably 40 to 70% by volume, calculated on the total mixture. For the production of a dispersion the mixture obtained is then brought into a zone of high turbulence.

To produce a zone of high turbulence common technical means are used, such as vessels with intense stirrer as well as tubular reactors with suitable stirring means and/or homogenization devices. The mixture can be added either discontinuously or, when suitable equipment is used, also continuously. The temperature during dispersion can be kept constant but it can also be varied after definite periods of time. Preferably, it should be in the range of from 10° to 80° C., more preferably 20° to 60° C. In this manner a dispersion of the water-insoluble phase in the aqueous polyvinyl alcohol solution can be produced in which the droplets formed have a diameter of from 1 to 50, preferably 5 to 10 $\mu$m, depending on the intensity of stirring or dispersion.

During stirring of the dispersion, disturbing foam may be formed in some cases, but this can be substantially suppressed by adding a suitable antifoaming agent, for example triisobutyl phosphate.

If it is desirable and suitable to adjust to a definite pH this can be done prior to, during or after dispersion. In most cases, however, such a procedure is unnecessary.

To isolate the microcapsules according to the invention, the dispersion is dehydrated in suitable manner, whereby the encapsulating material is deposited in the form of a uniform polyvinyl alcohol film on the surface of the liquid, water-insoluble substance particles to be encapsulated. To this end, it proved particularly advantageous to atomize the dispersion into a stream of heated air according to the principle of spray drying. It should be kept in mind, however, that the capability of being redissolved of the PVA film is distinctly reduced if the temperature is too high. It is, therefore, expedient to operate at inlet temperatures of from 120° to 150° C. and outlet temperatures of from 40° to 60° C., while taking care that the dried microcapsules separate as completely as possible in cyclones and are not heated to high temperatures for prolonged periods of time on the walls of the dryer. To avoid agglomeration it may be advantageous to add during spray drying small amounts of highly disperse silicic acid. The drying process as described above makes it possible to dehydrate the PVA encapsulation material to a degree of residual moisture of less than 0.5% by weight. It was surprising and could not be expected that the removal of water by spray drying exclusively yields products in capsule form without any formation of coherent coagulations of PVA which would mean losses.

Depending on the conditions of production, the powdery product obtained consists of microcapsules with liquid, water-insoluble content and having particle diameters of from about 1 to 20 $\mu$m. The product has satisfactory flow properties and the proportion of content amounts preferably to 10 to 90% by weight, more preferably 40 to 80% by weight. It has been ascertained that the properties of the microcapsules remained substantially unaltered after a 3 month storage at room temperature and at 50° C.

It is surprising that by the process of the invention active substances that are difficult to formulate or that cannot be formulated by known methods to give stable emulsion concentrates, can be transformed into ready manipulatable powdery capsule formulations which, for the practical application of the active substance, can be solvatized within a few minutes by simple dispersion in water and can form very stable emulsion concentrates as well as very stable emulsions ready for use. It is surprising that the dissolved wall material acts as wetting and dispersing or emulsifying agent and that no additional emulsifying agent need be added.

By adding further wetting agents, dispersants and/or emulsifiers it is likewise possible to prepare, with the microcapsules of the invention, formulations for specific applications.

Hence, the process according to the invention is especially suitable for encapsulating active ingredients for use in the field of plant protection, to combat pests and in the chemical technical field.

Pesticides suitable for encapsulation are especially all liquid pesticides or pesticides that are soluble in an organic solvent, which, or the solutions of which, are immiscible with water and the boiling points of which are above the boiling point of water.

Fungicides that can be used are, for example, Benomyl, Binapacryl, Captafol, Carbendazim, Dicloran, Fentin acetate, Folpet, Methomyl, Pyracarbolide, Quintozene, Thiabendazol, Triadimefon, and Tridemorph.

Suitable herbicides are, for example, Alachlor, Atrazin, Desmetryl, Dichlorprop, Dinoseb acetate, Diuron, Ioxynil, Linuron, Monolinuron, Monuron, and Quinon amide.

As insecticides there are mentioned, by way of examples, Carbaryl, Chlorpyrifos, Diazinon, Dichlorvos, Dimethoate, Endosulfan, Heptenophos, Malathion, Methyl parathion, Pirimicarb, Pyrazophos and Triazophos.

The following examples illustrate the invention.

EXAMPLE 1

140 g of polyvinyl alcohol obtained by partial hydrolysis of polyvinyl acetate and having a viscosity of 3 cP, measured in a 4% aqueous solution at 20° C. according to DIN 53 015, and a degree of hydrolysis of 83 mol % are dissolved in 420 g of water and, while vigorously stirring, a solution of 225 g of Pyrazophos (2-(0,0-diethylthionophosphoryl)-5-methyl-6-carbethoxy-pyrazolo[1,5a]pyrimidine) in 85 g of methyl naphthalene are added. The mixture is dispersed for 2 minutes in an intense stirrer of the type ® Ultra-Turrax T 45 at about 5,000 revolutions per minute and for dehydration it is atomized through a nozzle into a laboratory atomizing drier having a vaporization capacity of 3 kg/hr. The atomization takes place under a pressure of 3 atmospheres gauge. The air inlet temperature is from 145° to 148° C. and the temperature of the off-air before the cyclone ranges from 50° to 55° C. About 30 m³/hr of air are used.

In the cyclone there are collected 405 g of a dry powder of microcapsules having good flow properties and a diameter of the particles of 1 to 20 μm. The powder has an apparent density of 33 g/100 ml and a compacted apparent density of 38 g/100 ml. The Pyrazophos content of the microcapsules amounts to 45% by weight, the residual moisture content is equal to or smaller than 0.5% by weight.

EXAMPLE 2

140 g of polyvinyl alcohol of the type specified in Example 1 are dissolved in 420 g of water and, under the conditions listed in Example 1, a solution of 200 g of Endosulfan (6,7,8,9,10,10-hexachloro-1,5,5a,9a-tetrahydro-6,9-methano-2,3,4-benzo-dioxathiepin-3-oxide) in 120 g of methyl naphthalene heated to 50° C. is dispersed therein. After drying the dispersion by atomization as described in Example 1, 410 g of a dry, freely flowing powder of microcapsules having a diameter of 1 to 20 μm and an apparent density and compacted apparent density of 29 and 35 g/100 ml. are obtained. The Endosulfan content of the microcapsules amounts to 42% by weight, the residual moisture content is equal to or smaller than 0.5% by weight.

EXAMPLE 3

240 g of polyvinyl alcohol having a viscosity of 4 cp, measured in a 4% aqueous solution at 20° C. according to DIN 53 015, and a degree of hydrolysis of 88 mol % are dissolved in 960 g of water and, under the conditions indicated in Example 1, a solution of 280 g of Dinoseb acetate (2-sec.butyl-4,6-dinitrophenyl acetate) in 200 g of 4-methylcyclohexanone are dispersed in the solution obtained. After drying the dispersion by atomization as described in Example 1, 655 g of a dry, readily flowing powder of microcapsules are obtained having an apparent density and compacted apparent density of 39 and 44 g/100 ml, respectively. The proportion of Dinoseb acetate in the microcapsules amounts to 36% by weight, the residual moisture content being at most 0.5% by, weight.

EXAMPLE 4

210 g of polyvinyl alcohol of the type specified in Example 3 are dissolved in 800 g of water and, under the conditions of Example 1, a solution of 300 g of Triazophos (0,0-diethyl-(1-phenyl-1,2,4-triazol-3-yl)-thionophosphate) in 100 g of methylnaphthalene is dispersed in the solution obtained. After drying the dispersion by atomization under the conditions of Example 1, 550 g of a dry, readily flowing powder having an apparent density and a compacted apparent density of 32 and 37 g/100 ml, respectively, are obtained. The proportion of Triazophos in the microcapsules amounts to 48% by weight, the residual moisture content being at most 0.5% by weight.

We claim:

1. Process for microencapsulating a water-insoluble liquid in a water-soluble polyvinyl alcohol shell which comprises dispersing from 20 to 80% by volume of said liquid in from 80 to 20% by volume of an aqueous polyvinyl alcohol solution containing from 2 to 50% by weight of polyvinyl alcohol obtained by partial hydrolysis of polyvinyl acetate and having a degree of hydrolysis of from 72 to 99 mol % and a viscosity of from 2 to 18 cP, measured in a 4% aqueous solution at 20° C., and spray drying the resulting dispersion at a temperature between about 40° and 150° C. to a residual moisture content of less than about 0.5% by weight.

2. The process of claim 1, wherein the polyvinyl alcohol has a degree of hydrolysis of 83 to 88 mol % and a viscosity from 3 to 5 cP, measured in a 4% aqueous solution at 20° C.

3. The process of claim 1, wherein the aqueous polyvinyl alcohol solution additionally contains from 2 to 50% by weight of polyethylene glycol, glycerol or trimethylol propane.

4. The process of claim 1, wherein the water-insoluble liquid and/or the aqueous solution additionally contain wetting agents, dispersing agents and/or emulsifiers.

5. The process of claim 1, wherein the water-insoluble liquid contains at least one pesticide and optionally a solvent.

6. The process of claim 1, wherein the water-insoluble liquid is dispersed in the aqueous solution at a temperature in the range of from 10° to 80° C.

7. The process of claim 1, wherein the water-insoluble phase has a boiling point above that of water and the dispersion is dehydrated by spray drying.

8. The process of claim 7, wherein the dispersion is spray-dried at air inlet temperatures of from 120° to 150° C., optionally with the addition of highly disperse silicic acid.

* * * * *